(12) United States Patent
Alvaro et al.

(10) Patent No.: US 7,655,693 B2
(45) Date of Patent: Feb. 2, 2010

(54) COMPOUNDS

(75) Inventors: Giuseppe Alvaro, Verona (IT); Markus Bergauer, Verona (IT); Roberto Profeta, Verona (IT); Riccardo Giovannini, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 282 days.

(21) Appl. No.: 11/570,560

(22) PCT Filed: Oct. 6, 2006

(86) PCT No.: PCT/EP2006/009731

§ 371 (c)(1),
(2), (4) Date: Dec. 13, 2006

(87) PCT Pub. No.: WO2007/042239

PCT Pub. Date: Apr. 19, 2007

(65) Prior Publication Data

US 2008/0280969 A1 Nov. 13, 2008

(30) Foreign Application Priority Data

| Oct. 10, 2005 | (GB) | ................................ | 0520581.0 |
| Nov. 11, 2005 | (GB) | ................................ | 0523045.3 |
| Feb. 27, 2006 | (GB) | ................................ | 0603900.2 |
| Sep. 18, 2006 | (GB) | ................................ | 0618336.2 |

(51) Int. Cl.
*A61K 31/401* (2006.01)

(52) U.S. Cl. ..................................... 514/423; 548/537

(58) Field of Classification Search ................. 514/423; 548/537

See application file for complete search history.

(56) References Cited

U.S. PATENT DOCUMENTS

| 5,236,957 | A | 8/1993 | Dostert et al. |
| 6,201,016 | B1 | 3/2001 | Cai et al. |
| 6,306,903 | B1 | 10/2001 | Pevarello et al. |
| 6,951,861 | B1 | 10/2005 | Alvaro et al. |
| 2004/0097578 | A1 | 5/2004 | Jolidon et al. |
| 2004/0235752 | A1 | 11/2004 | Pitt et al. |
| 2005/0234065 | A1 | 10/2005 | Hulin et al. |
| 2008/0269208 | A1 | 10/2008 | Alvaro et al. |
| 2008/0293753 | A1 | 11/2008 | Alvaro et al. |

FOREIGN PATENT DOCUMENTS

| WO | 0057877 A1 | 10/2000 |
| WO | 2004026826 A1 | 4/2004 |
| WO | 2004/083189 | 9/2004 |
| WO | 2004/092140 | 10/2004 |
| WO | 2004/094395 | 11/2004 |
| WO | 2005/000309 | 1/2005 |
| WO | 2005040108 A1 | 5/2005 |
| WO | WO 2006119390 A1 | 11/2006 |
| WO | WO 2006119451 A1 | 11/2006 |
| WO | WO 2006124865 A2 | 11/2006 |
| WO | WO 2008090114 A1 | 7/2008 |
| WO | WO 2008090115 A1 | 7/2008 |
| WO | WO 2008090116 A1 | 7/2008 |
| WO | WO 2008090117 A1 | 7/2008 |
| WO | WO 2008122546 A1 | 10/2008 |

OTHER PUBLICATIONS

Vippagunta et al., Crystalline Solids, Advanced Drug Delivery Reviews, vol. 48, p. 3-26 (2001).*
Gavezzotti et al. Are Crystal Structures Predictable?, Accounts of Chemical Research, vol. 27, p. 309-314 (1994).*
Wolff, M. "Burger's Medicinal Chemistry, 5edt Part I", John Wiley & Sons, 1995, p. 975-977.*
Banker et al. Modern pharmaceutics, 3Ed., Marcel Dekker, New York, 1996, p. 451 and 596.*

* cited by examiner

*Primary Examiner*—Kamal A Saeed
*Assistant Examiner*—Valerie Rodriguez-Garcia
(74) *Attorney, Agent, or Firm*—Alice P. Bradney; Kathryn L. Coulter

(57) ABSTRACT

The invention provides a compound of formula (I), pharmaceutical compositions thereof, and methods of treatment using the same.

(I)

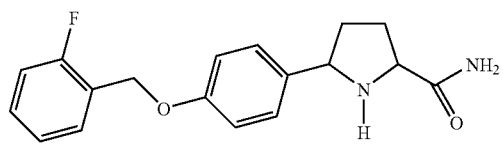

14 Claims, No Drawings

COMPOUNDS

This application is filed pursuant to 35 U.S.C. § 371 as a United States National Phase Application of International Patent Application Serial No. PCT/EP2006/009731 filed Oct. 6, 2006, which claims priority from Great Britain Application No. 0520581.2 filed in the United Kingdom on Oct. 10, 2005, Great Britain Application No. 0523045.3 filed in the United Kingdom on Nov. 11, 2005, Great Britain Application No. 0603900.2 filed in the United Kingdom on Feb. 27, 2006, and Great Britain Application No. 0618336.2 filed in the United Kingdom on Sep. 18, 2006, the content of each of which is incorporated herein by reference.

The present invention relates to an α-aminocarboxyamide derivative, salts and prodrugs thereof, and to the use of this derivative, salts and prodrugs thereof in treating diseases and conditions mediated by modulation of use-dependent voltage-gated sodium channels. In addition, the invention relates to compositions containing this derivative, salts and prodrugs thereof, and processes for their preparation.

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Drugs, such as lidocaine, that block voltage-gated sodium channels are used as local anesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anesthetics, regional block of sodium channels on sensory neurons prevents the conduction of painful stimuli. A key feature of these drugs is their use-dependent mechanism of action. The drugs are thought to stabilise an inactivated configuration of the channel that is adopted rapidly after the channel opens. This inactivated state provides a refractory period before the channel returns to its resting (closed) state ready to be reactivated. As a result, use-dependent sodium channel blockers retard the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for use-dependent sodium channel blockers is highly conserved between all the subtypes. As a result, drugs such as lidocaine, lamotrigine and carbamazepine do not distinguish between the subtypes. However, selectivity can be achieved as a result of the different frequencies at which the channels normally operate.

Drugs that block voltage-gated sodium channels in a use-dependent manner are also used in the treatment of bipolar disorder, either to reduce symptoms of mania or depression, or as mood stabilisers to prevent the emergence of mood episodes. Clinical and preclinical evidence also suggests that use-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of use-dependent sodium channel inhibition in key brain areas, such as the frontal cortex. However, interaction with voltage-gated calcium channels may also contribute to the efficacy of these drugs.

International published patent application WO05/000309 (Ionix Pharmaceuticals Limited) discloses the use of compounds of formula (I), wherein $R_1$ is an organic substituent, $X_1$ and $X_2$ are direct bonds or spacer moieties, Ar is aryl or heteroaryl and Y is a substituted aminoalkyl group or a heteroaryl-, heterocyclyl- or phenyl-containing moiety:

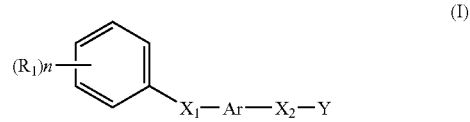

(I)

Such compounds are inhibitors of sensory neurone specific sodium channels and are said to be useful in the treatment of chronic and acute pain, tinnitus, bowel disorders, bladder dysfunction and demyelinating diseases.

International published patent application WO04/083189 (Merck & Co.) discloses biaryl substituted triazole compounds of formula (I), (II) and (III) as sodium channel blockers:

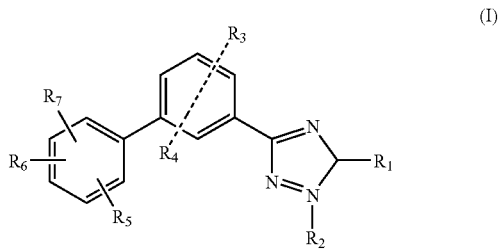

(I)

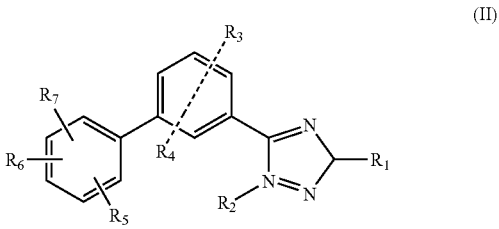

(II)

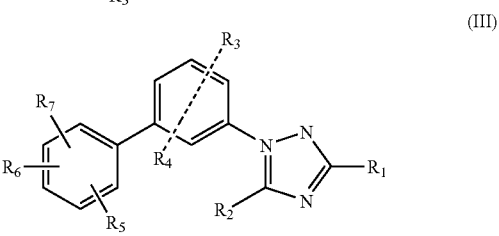

(III)

Such compounds are said to be useful in the treatment of conditions associated with sodium channel activity including, for example, acute pain, chronic pain, visceral pain, epilepsy, irritable bowel syndrome, depression and others.

International published patent application WO04/092140 (Merck & Co.) discloses biaryl substituted pyrazoles of formula (I), (II), (III) and (IV) as sodium channel blockers:

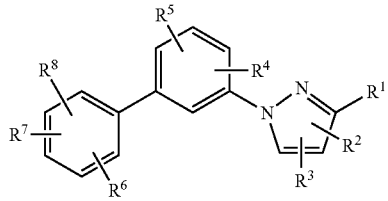

(I)

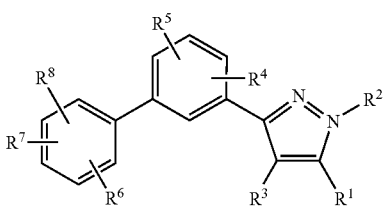

(II)

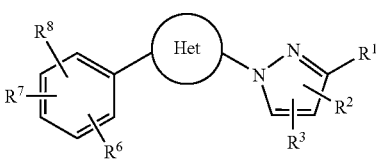

(III)

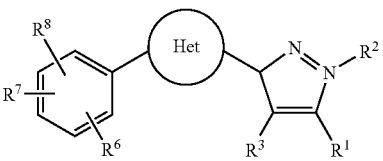

(IV)

The compounds are said to be useful in the treatment of conditions including acute pain, chronic pain, visceral pain, inflammatory pain and neuropathic pain.

International published patent application WO04/094395 (Merck & Co.) discloses birayl substituted thiazoles, oxazoles and imidazoles of formula (I) as sodium channel blockers:

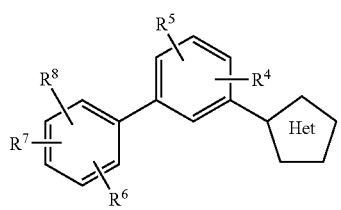

(I)

The compounds are said to be useful in the treatment of conditions including acute pain, chronic pain, visceral pain, inflammatory pain and neuropathic pain.

International patent application WO04/026826 (F. Hoffman La Roche A G) discloses 4-pyrrolidinophenyl-benzyl ether derivatives of formula (I):

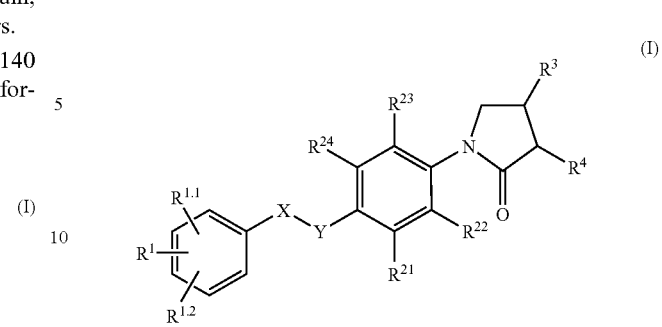

(I)

The compounds are said to be monoamine oxidase B inhibitors and are said to be useful in the treatment of conditions such as Alzheimer's disease or senile dementia.

The object of the present invention is to identify a compound which modulates voltage-gated sodium channels.

In one embodiment, the compound will be a use dependent sodium channel inhibitor.

In another embodiment, the compound will be a subtype NaV1.3 sodium channel use dependent inhibitor.

Another object of the invention is to identify a use dependent sodium channel inhibitor which has a suitable developability profile, for example in terms of exposure (Cmax) and/or bioavailability on oral administration.

According to a first aspect, the invention provides 5-(4-{[(2-fluorophenyl)methyl]oxy}phenyl)-prolinamide of formula (I),

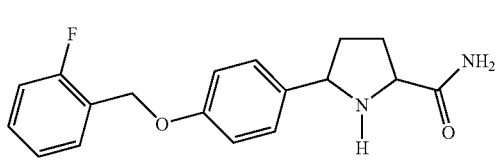

(I)

or a pharmaceutically acceptable salt, a solvate or prodrug thereof.

Hereinafter, the compound of formula (I), its pharmaceutically acceptable salts, solvates and its prodrugs, defined in any aspect of the invention (except intermediate compounds in chemical processes) are referred to as "the compounds of the invention".

It will be appreciated by the person skilled in the art that the compound of formula (I) may exist as four possible diastereoisomers. In a further embodiment, the compound of the invention is selected from the list consisting of:

(5R)-5-(4-{[(2-fluorophenyl)methyl]oxy}phenyl)-L-prolinamide (Ia),

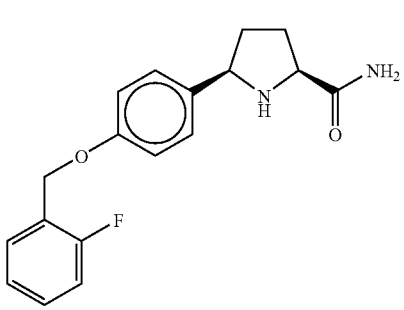

(Ia)

(5S)-5-(4-{[(2-fluorophenyl)methyl]oxy}phenyl)-D-prolinamide (Ib),

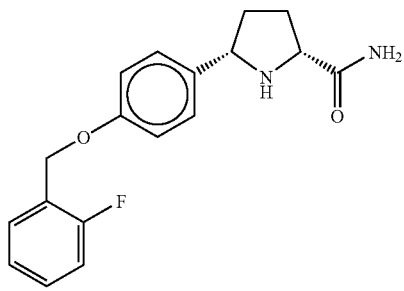

(5R)-5-(4-{[(2-fluorophenyl)methyl]oxy}phenyl)-D-prolinamide (Ic)

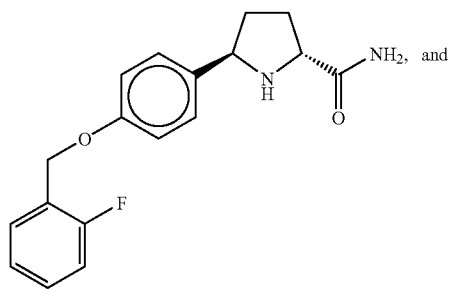

(5S)-5(4-{[(2-fluorophenyl)methyl]oxy}phenyl)-L-prolinamide (Id)

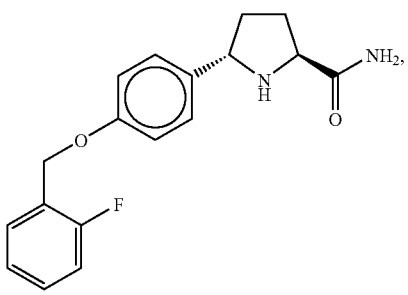

and pharmaceutically acceptable salts, solvates or prodrugs of (Ia), (Ib), (Ic) or (Id).

In a further embodiment the compound of the invention is (5R)-5-(4-{[(2-fluorophenyl)methyl]oxy}phenyl)-L-prolinamide (Ia), or a pharmaceutically acceptable salt, solvate or prodrug thereof.

The diastereoisomers of the compound of formula (I) may be obtained according to methods well known in the literature, for example by preparative HPLC or by chromatographic purifications. A racemic mixture may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compound of formula (I) may form pharmaceutically or veterinarily acceptable salts. The pharmaceutically or veterinarily acceptable salts of the compound of formula (I) which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

It will be appreciated by those skilled in the art that certain protected derivatives of the compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

The pharmaceutically acceptable solvates of the compounds of the invention include hydrates thereof.

Also included within the scope of the compounds of the invention are polymorphs thereof.

The compounds of the invention may exist in one or more tautomeric forms. All tautomers and mixtures thereof are included in the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

According to a further aspect, the invention provides a process to prepare a compound of formula (I) comprising the reaction of a compound of formula (II)

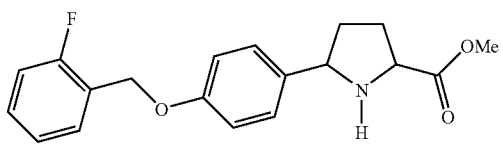

(II)

with a solution of ammonia in a suitable solvent.

In one embodiment, the solvent is methanol. In a further embodiment the solution of ammonia in methanol is concentrated, for example a 7N or 11.2 M solution.

In another embodiment the reaction is performed at room temperature.

As discussed hereinabove, it is believed that compounds of the invention may be useful for the treatment of diseases and conditions mediated by modulation of voltage-gated sodium channels.

Therefore, according to a further aspect, the invention provides compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

Without wishing to be bound by theory, diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-induced Persisting Dementia, Alcohol-Induced Persisting Amnestic Disorder, Alcohol-Induced Psychotic Disorder, Alcohol-induced Mood Disorder, Alcohol-induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-induced Mood Disorder, Amphetamine-induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-induced Psychotic Disorder, Cocaine-Induced Mood Disorder, Cocaine-induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencydidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vii) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

viii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

ix) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

x) Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9): and xi) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73). Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xii) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

In an embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegenerabon such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other [antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like].

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 800 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects.

i) A compound of the invention for use in treating or preventing a disease or condition mediated by modulation of voltage-gated sodium channels.

ii) A method of treatment or prevention of a disease or condition mediated by modulation of voltage-gated sodium channels in a mammal comprising administering an effective amount of a compound of the invention.

iii) Use of a compound of the invention in the manufacture of a medicament to treat or prevent a disease or condition mediated by modulation of voltage-gated sodium channels.

iv) Use of a compound of the invention to treat or prevent a disease or condition mediated by modulation of voltage-gated sodium channels.

EXPERIMENTALS

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The compounds described in the Examples described hereinafter have all been prepared as a first step from stereochemically pure methyl 5-oxo-L-prolinate or ethyl 5-oxo-D-prolinate, for example 99% ee. The stereochemistry of the compounds of the Descriptions and Examples have been assigned on the assumption that the pure configuration of 5-oxo-prolinate is maintained throughout any subsequent reaction conditions.

The absolute configuration of the stereocenter at the 2-position as shown below the has been assigned on the basis of NOE $^1$H NMR experiments, by determining the relative stereochemistry of this stereocenter with respect to the one at the 5-position.

(I)

Compounds are named using ACD/Name PRO6.02 chemical naming software (Advanced Chemistry Development Inc., Toronto, Ontario, M5H2L3, Canada).

Proton Magnetic Resonance (NMR) spectra are typically recorded either on Varian instruments at 300, 400, 500 or 600 MHz, or on a Bruker instrument at 300 MHz and 400 MHz. Chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer was detected the chemical shifts for the most abundant one is reported.

HPLC analysis indicated by $R_t$(HPLC): ×min, was performed on an Agilent 1100 series instrument using a Luna 3u C18(2) 100 A (50×2.0 mm) column (mobile phase: 100% [water+0.05% TFA] to 95% [acetonitrile+0.05% TFA] in 8 min, flux 1 ml/min, detection wavelength 220 nm.

Mass spectra (MS) are typically taken on a 4 II triple quadrupole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS–ES (+): analysis performed on a Supelcosil ABZ +Plus (33×4.6 mm, 3 µm) (mobile phase: 100% [water+0.1% HCO$_2$H] for 1 min, then from 100% [water+0.1% HCO$_2$H] to 5% [water+0.1% HCO$_2$H] and 95% [CH$_3$CN] in 5 min, finally under these conditions for 2 min; T=40° C.; flux=1 mL/min; LC/MS–ES (−): analysis performed on a Supelcosil ABZ +Plus (33×4.6 mm, 3 µm) (mobile phase: 100% [water+ 0.05% NH$_3$] for 1 min, then from 100% [water+0.05% NH$_3$ to 5% [water+0.05% NH$_3$] and 95% [CH$_3$CN] in 5 min, finally under these conditions for 2 min; T=40° C.; flux=1 mL/min]. In the mass spectra only one peak in the molecular ion cluster is reported.

The optical rotation was measured on a JASCO DIP-360 digital polarimeter (λ=589 nm, T=20° C., c=1 in MeOH).

Flash silica gel chromatography are typically carried out on silica gel 230-400 mesh (supplied by Merck AG Darrnstadt, Germany) or over Varian Mega Be—Si pre-packed cartridges or over pre-packed Biotage silica cartridges.

SPE-SCX cartridges are ion exchange solid phase extraction columns by supplied by Varian. The eluent used with SPE-SCX cartridges is methanol followed by 2N ammonia solution in methanol.

In a number of preparation purification was performed using either Biotage manual flash chromatography (Flash+) or automatic flash chromatography (Horizon) systems. All these instruments work with Biotage Silica cartridge.

SPE-Si cartridges are silica solid phase extraction columns supplied by Varian.

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0° 2θ, end angle: 45.0° 2θ, step size: 0.02° 2θ, time per step: I seconds. The sample was prepared on zero background sample holder.

Differential Scanning Calorimetry (DSC): It should be recognized that the endotherm peak as measured is dependent under a number of factors including the machine employed, the rate of heating, the calibration standard, humidity and the purity of the sample used.

Melting points reported in the experimentals are estimated on the basis of the onset of endotherm peaks registered during DSC analysis.

The following table lists the abbreviations used:

BOC2O bis(1,1-dimethylethyl)dicarbonate

DCM—dichloromethane

DIPEA—diisopropylethylamine

DMAP—4-(dimethylamino)pyridine

DMF—dimethylformamide   O-(benzotriazol-1-yl)-N,N, N'N'-tetramethyluronium

TBTU—tetrafluoroborate

THF—tetrahydrofuran

TFA trifluoroacetic acid

MTBE methyl-t-butyl ether

Et2O Diethyl ether

AcOEt Ethyl acetate

MeOH Methyl alcohol

DMSO Dimethyl sulfoxide

Description 1: 1-(1,1-dimethylethyl) 2-methyl (2S)-5-oxo-1,2-pyrrolidinedicarboxylate (D1)

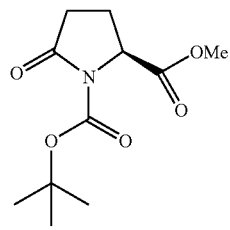

To a solution of commercially available methyl 5-oxo-L-prolinate (20 g, 140 mmol) in DCM (200 ml) were added triethylamine (19.6 ml, 140 mmol), DMAP (17.2 g, 140 mmol) and then dropwise a solution of BOC$_2$O (61 g, 280 mmol) in DCM (100 ml). The resulting red mixture was stirred at room temperature for 2 hours. Then the solvent was removed under reduced pressure and the crude material was purified by chromatography on silica gel eluting with cyclohexane/ethyl acetate (7:3 to 4:6) to afford (after a trituration in hexane/diethylether 1:1) the title compound as a white solid (32.4 g, 96%); R$_f$ (cyclohexanes:ethyl acetate=65:35): 0.21; $^1$H NMR (300 MHz, CDCl$_3$) δ (ppm): 4.62 (dd, 1H), 3.78 (s, 3H), 2.68-2.58 (m, 1H), 2.52-2.45 (m, 1H), 2.37-2.27 (m, 1H), 2.08-1.97 (m, 1H), 1.48 (s, 9H).

Description 2: methyl (2S)-2-({[(1,1-dimethylethyl)oxy]carbonyl}amino)-5-oxo-5-{4-[(phenylmethyl)oxy]phenyl}pentanoate (D2)

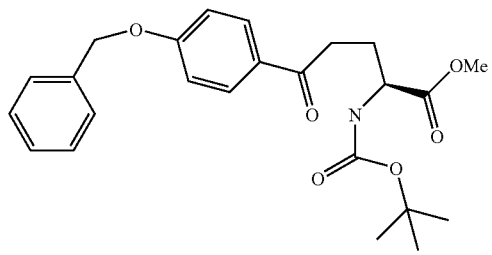

n-Butyl lithium 1.6M solution in hexanes (0.88 ml, 1.4 mmol) was added dropwise to a solution of commercially available 1-bromo-4-[(phenylmethyl)oxy]benzene (390 mg, 1.48 mmol) in dry THF (2 ml) at −78° C. under nitrogen atmosphere. The resulting suspension was stirred at −78° C. for 40 minutes and then it was added dropwise to a solution of 1-(1,1-dimethylethyl) 2-methyl (2S)-5-oxo-1,2-pyrrolidinedicarboxylate (D1, 300 mg, 1.23 mmol) in dry THF (2.4 ml) previously cooled to −78° C. The mixture was stirred at −78° C. for 40 minutes and at 40° C. for 1 h, then it was quenched at −40° C. with an aqueous saturated ammonium chloride solution. The mixture was diluted with water and extracted with ethyl acetate. The organic phase was then washed with brine, dried over Na$_2$SO$_4$, and evaporated under reduced pressure to give the crude material, which was purified by chromatography on silica gel eluting with cyclohexane/ethylacetate (95:5), thus affording the title compound as a white solid (170 mg, 32%); R$_f$ (cyclohexane:ethyl acetate=8:2): 0.30; $^1$HNMR (300 MHz, CDCl$_3$) δ(ppm): 7.95 (d, 2H), 7.50-7.33 (m, 5H), 7.03 (d, 2H), 5.20 (bs, 1H), 5.15 (s, 2H), 4.45-4.35 (m, 1H), 3.78 (s, 3H), 3.15-2.95 (m, 2H), 2.36-2.26 (m, 1H), 2.16-2.02 (m, 1H), 1.45 (s, 9H).

Description 3: methyl (2S)-5-{4-[(phenylmethyl)oxy]phenyl}-3,4-dihydro-2H-pyrrole-2-carboxylate (D3)

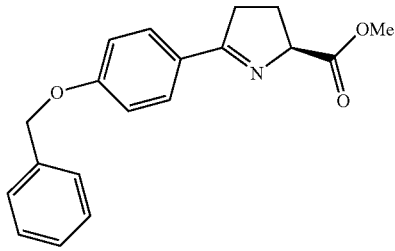

To a solution of methyl (2S)-2-({[(1,1-dimethylethyl)oxy]carbonyl}amino)-5-oxo-5-{4-[(phenylmethyl)oxy]phenyl}pentanoate (D2, 323 mg, 0.75 mmol) in dry DCM (4 ml) at 0° C., under nitrogen atmosphere was added trifluoroacetic acid (1 ml) dropwise. The resulting pale pink solution was allowed to warm to room temperature over 1 hour, then it was evaporated under reduced pressure, affording the title compound (D7, 291 mg, 0.68 mmol, 91%) as a greenish oil which may be used in the next step without any further purification; R$_t$ (HPLC): 3.69 min; MS: (ES/+) m/z: 310 [MH$^+$], C19H19NO3 requires 309.

Description 4: methyl (5R)-5-{4-[(phenylmethyl)oxy]phenyl}-L-prolinate (D4)

Description 5: methyl (5S)-5-{4-[(phenylmethyl)oxy]phenyl}-L-prolinate (D5)

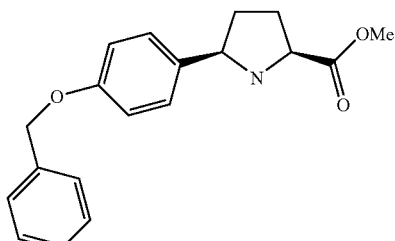

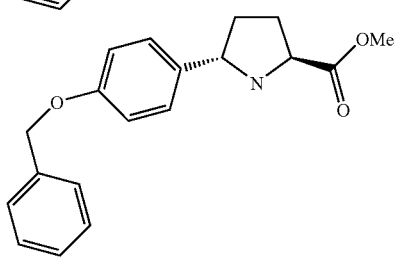

To a solution of methyl (2S)-5-{4-[(phenylmethyl)oxy]phenyl}-3,4-dihydro-2H-pyrrole-2-carboxylate (D3, 13.7 g, 32.4 mmol) in MeOH (200 ml) was added PtO$_2$ (240 mg) and the mixture was stirred under a hydrogen atmosphere (2 atmos) for 6 hours. Then the catalyst was filtered off and the solvent removed under reduced pressure to give a red oil which was dissolved in ethyl acetate and washed with NaHCO₃ solution. The resulting crude material was purified by chromatography on silica gel eluting with cyclohexane/ethyl acetate (9:1 to 8:2) to afford the title compounds:

D4, 4.15 g, 13.3 mmol, Y=41%. MS: (ES/+) m/z: 312 [MH⁺]. C19H21NO3 requires 311. Rt (HPLC): 3.80 min. Rf (cyclohexane:ethyl acetate=7:3): 0.18. ¹HNMR (300 MHz, CDCl₃) δ(ppm): 7.40 (d, 2H); 7.35 (t, 2H); 7.33 (d, 2H); 7.29 (t, 1H); 6.93 (d, 2H); 5.03 (s, 2H); 4.23 (dd, 1H); 4.00 (dd, 1H); 3.71-3.79 (m, 3H); 2.18-2.30 (m, 1H); 2.09-2.18 (m, 2H); 1.67-1.78 (m, 1H). NOE between the proton at C2 and the proton at C5 could be observed.

D5, 0.6 g, 1.9 mmol, Y=6%. MS: (ES/+) m/z: 312 [MH⁺]. C19H21NO3 requires 311; Rt (HPLC): 3.73 min. Rf (cyclohexane:ethyl acetate=7:3): 0.32. ¹HNMR (300 MHz, CDCl₃) δ(ppm): 7.40 (d, 2H); 7.35 (t, 2H); 7.29 (d, 2H); 7.28 (t, 1H); 6.91 (d, 2H); 4.97-5.07 (m, 2H); 4.29 (dd, 1H); 4.09 (dd, 1H); 3.71-3.75 (m, 3H); 2.29-2.42 (m, 1H); 2.09-2.20 (m, 1H); 1.90-2.02 (m, 1H); 1.69-1.82 (m, 1H). NOE between the proton at C2 and the proton at C5 was not observed.

Description 6: (5R)-5-{4-[(phenylmethyl)oxy]phenyl}-L-proline (D6)

Description 7: (5R)-1-{[(1,1-dimethylethyl)oxy]carbonyl}-5-{4-[(phenylmethyl)oxy]phenyl}-L-proline (D7)

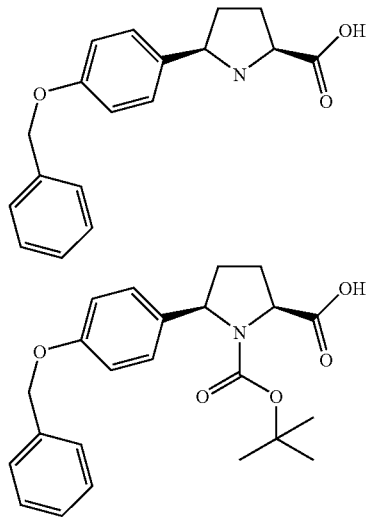

To a solution of methyl (5R)-5-{4-[(phenylmethyl)oxy]phenyl}-L-prolinate (D4, 120 mg, 0.38 mmol) in THF (2.3 ml) was added LiOH monohydrate (26 mg, 0.61 mmol) dissolved in water (1.1 ml), followed by methanol (1.1 ml). The resulting solution was stirred at room temperature for 2.5 hours, then left overnight at −18° C. Then the organic solvent was evaporated under reduced pressure maintaining the temperature at 38° C. and the aqueous residue containing the acid intermediate (D6, Rt (HPLC)=3.63 min. MS: (ES/+) m/z: 298 [MH⁺]. C18H19NO3 requires 297) was treated with BOC₂O (168 mg, 0.77 mmol) dissolved in THF (1.1 ml). The reaction mixture was stirred at room temperature for 3.5 hours. The organic solvent was evaporated and the basic aqueous solution was acidified at 0° C. with aqueous 1N HCl solution to pH=3, this acidic aqueous solution was extracted with ethyl acetate (2×10 ml). The organic phase dried over Na₂SO₄ and evaporated under reduced pressure gave a solid, which was titurated in n-hexanes (3×6 ml) affording the title compound as a white powder (D7, 137 mg, 90% for two steps); Rt (HPLC): 5.81 min; Rf (cyclohexane:ethyl acetate=1:1): 0.34; MS: (ES/+) m/z: 420 [M+Na⁺] C23H27NO5 requires 397; MS: (ES/−) m/z: 396 [M−H] C23H27NO5 requires 397; ¹H NMR (300 MHz, CDCl₃) δ (ppm): 7.5-7.3 (m, 5H), 7.10 (bm, 2H), 6.90 (d, 2H), 5.08 (s, 2H), 4.65 (bm, 1H), 4.50 (bm, 1H), 2.58 (bm, 1H), 2.31 (bm, 1H), 2.11-1.90 (m, 2H), 1.16 (s, 9H).

Description 8: 1,1-dimethylethyl (2S,5R)-2-(aminocarbonyl)-5-{4-[(phenylmethyl)oxy]phenyl}-1-pyrrolidinecarboxylate (D8)

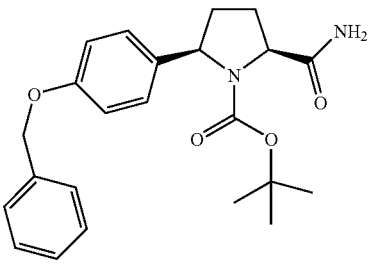

To a solution of (5R)-1-{[(1,1-dimethylethyl)oxy]carbonyl}-5-{4-[(phenylmethyl)oxy]phenyl}-L-proline (D7, 1.44 g, 3.62 mmol) in dry DMF (20 ml) were added DIPEA (1.26 ml, 7.24 mmol), then TBTU (1.23 g, 3.98 mmol) and after 20 minutes, 1,1,1,3,3,3-hexamethyldisilazane (1.15 ml, 5.43 mmol). The reaction mixture was stirred at room temperature for 2 h, then it was treated with aqueous 5% NaHCO₃ solution (30 ml) and stirred for further 30 minutes. The resulting mixture was diluted with water and extracted with ethyl acetate. The organic phase was then washed twice with brine/ice, dried over Na₂SO₄ and evaporated to give a colourless oil. This crude material was purified by chromatography on silica gel eluting with cyclohexane/ethyl acetate (7:3 to 5:5) to afford the title compound (1.25 g, 87%); R_f (HPLC): 5.51 min; R_f (cyclohexane:ethyl acetate=1:1): 0.29. MS: (ES/+) m/z: 419 [M+Na⁺]; C23H28N2O4 requires 396.

Description 9: 1,1-dimethylethyl (2S,5R)-2-(aminocarbonyl)-5-(4-hydroxyphenyl)-1-pyrrolidinecarboxylate (D9)

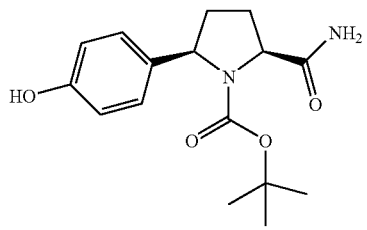

To a solution of 1,1-dimethylethyl (2S,5R)-2-(aminocarbonyl)-5-{4-[(phenylmethyl)oxy]phenyl}-1-pyrrolidinecarboxylate (D8, 1.2 g, 3.02 mmol) in methanol (25 ml) was added Pd/C 10% wt (210 mg) and the mixture was stirred under hydrogen (1 atm) for 6 hours. The catalyst was filtered off and the solvent removed under reduced pressure to give the title compound as a white solid (870 mg, 94%); R$_t$ (HPLC): 3.61 min; R$_f$ (cyclohexane:ethyl acetate=1:1): 0.18; MS: (ES/+) m/z: 329 [M+Na$^+$]. C16H22N2O4 requires 306; $^1$H NMR (300 MHz, d$_6$-DMSO) δ ppm: 9.15 (bs, 1H); 7.40 (bm, 2H); 7.30 (s, 1H); 6.90 (s, 1H); 6.65 (d, 2H); 4.50-4.80 (m, 1H); 4.05-4.28 (m, 1H); 2.07-2.24 (m, 1H); 1.95-2.07 (m, 1H); 1.60-1.89 (m, 2H); 1.00-1.45 (m, 9H).

Description 10: 1,1-dimethylethyl (2S,5R)-2-(aminocarbonyl)-5-(4-{[(2-fluorophenyl)methyl]oxy}phenyl)-1-pyrrolidinecarboxylate (D10)

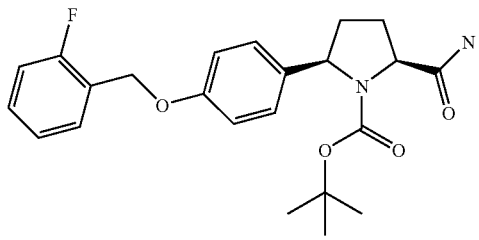

1-(Bromomethyl)-2-fluorobenzene (30 μl, 0.220 mmol) was added to a solution of 1,1-dimethylethyl (2S,5R)-2-(aminocarbonyl)-5-(4-hydroxyphenyl)-1-pyrrolidinecarboxylate (D9, 45 mg, 0.146 mmol) and potassium carbonate (30 mg, 0.217 mmol) in acetonitrile (2 ml). The mixture was stirred overnight at room temperature. After the reaction was finished, as shown by TLC, ethyl acetate and water were added. The organic phase was then washed with brine, dried (Na$_2$SO$_4$), filtered and evaporated. The crude material was purified by chromatography on silica gel using cyclohexane/ethyl acetate (7:3 to 6:4) to afford the title compound (51 mg, 85%); Rt (HPLC): 5.56 min; Rf (cyclohexane:ethyl acetate=1:1): 0.28; $^1$H NMR (300 MHz, CDCl$_3$) δ(ppm): 7.56-7.48 (m, 1H); 7.37-7.28 (m, 1H); 7.24-7.06 (m, 5H); 6.93 (d, 2H); 5.45-5.37 (br. s, 1H); 5.15 (s, 2H); 4.73-4.60 (m, 1H); 4.53-4.45 (m, 1H); 2.58-2.48 (m, 1H); 2.34-2.25 (m, 1H); 2.09-1.93 (m, 2H); 1.28-1.13 (br. s, 9H).

Description 11: (5S)-5-{4-[(phenylmethyl)oxy]phenyl}-L-proline (D11)

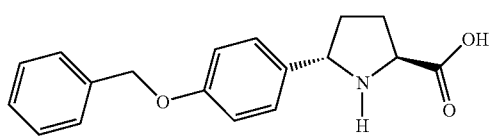

The title compound was synthesized following a similar procedure as set out earlier in Description 6 starting from methyl (5S)-5-{4-[(phenylmethyl)oxy]phenyl}-L-prolinate (D5, 600 mg, 1.92 mmol); Rt (HPLC): 3.66 min; MS: (ES/−) m/z: 296 [M−H]; MS: (ES/+) m/z: 298 [M+H], C18H19NO3 requires 297.

Description 12: (5S)-1-{[(1,1-dimethylethyl)oxy]carbonyl}-5-{4-[(phenylmethyl)oxy]phenyl}-L-proline (D12)

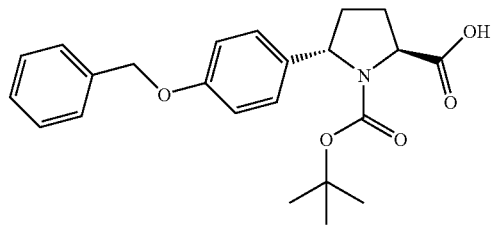

The title compound was synthesized (695 mg, 90% over two steps) a similar procedure as set out earlier in Description 7 starting from ((5S)-5-{4-[(phenylmethyl)oxy]phenyl}-L-proline (D11). The crude material may be used without any further purification in the next step; R$_t$ (HPLC): 5.72 min; MS: (ES/−) m/z: 396 [M−H]; MS: (ES/+) m/z: 420 [M+Na$^+$], C23H27NO5 requires 397, $^1$H NMR (400 MHz, DMSO-d6) δ(ppm): 12.70-12.42 (br. s, 1H); 7.47-7.42 (m, 2H); 7.42-7.35 (m, 2H); 7.35-7.29 (m, 1H); 7.13-7.07 (m, 2H); 6.98-6.92 (m, 2H); 5.08 and 5.06 (s, s, 2H); 4.96-4.91 and 4.86-4.81 (m, m, 1H); 4.44-4.40 and 4.39-4.34 (m, m, 1H); 2.36-2.13 (m, 2H); 1.90-1.80 (m, 1H); 1.69-1.57 (m, 1H); 1.33 and 1.09 (s, s, 9H).

Description 13: 1,1-dimethylethyl (2S,5S)-2-(aminocarbonyl)-5-{4-[(phenylmethyl)oxy]phenyl}-1-pyrrolidinecarboxylate (D13)

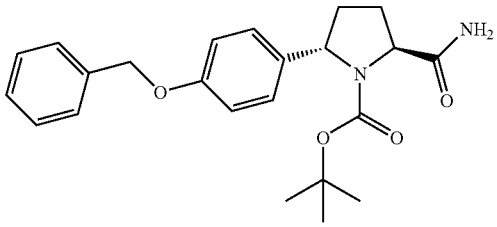

The title compound was synthesized (600 mg, 87%) following a similar procedure as set out earlier in Description 8 starting from (5S)-1-{[(1,1-dimethylethyl)oxy]carbonyl}-5-{4-[(phenylmethyl)oxy]phenyl}-L-proline (D12, 690 mg, crude material); R$_t$ (HPLC): 5.23 min; MS: (ES/+) m/z: 419 [M+Na$^+$], C23H28N2O4 requires 396.

Description 14: 1,1-dimethylethyl (2S,5S)-2-(aminocarbonyl)-5-(4-hydroxyphenyl)-1-pyrrolidinecarboxylate (D14)

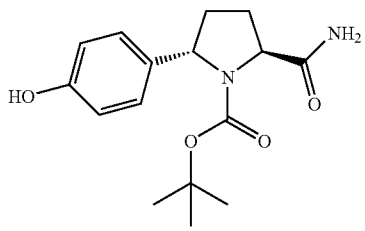

The title compound was synthesized (400 mg, 94%) following a similar procedure as set out earlier in Description 9 starting from 1,1-dimethylethyl (2S,5S)-2-(aminocarbonyl)-5-{4-[(phenylmethyl)oxy]phenyl}-1-pyrrolidinecarboxylate (D13, 550 mg, 1.38 mmol); Rt (HPLC): 3.14 min; MS: (ES/+) m/z: 329 [M+Na⁺], C16H22N2O4 requires 306; ¹H NMR (400 MHz, DMSO-d6) δ(ppm): 9.21 (br. s, 1H); 7.40-7.30 (br. s, 1H); 6.96-6.90 (m, 2H); 6.90-6.84 (br. s, 1H); 6.71-6.64 (m, 2H); 4.90 and 4.80 (d, d, 1H); 4.32 and 4.25 (d, d, 1H); 2.37-2.02 (m, 2H); 1.78-1.70 (m, 1H); 1.61-1.46 (m, 1H); 1.32 and 1.09 (s, s, 9H).

Description 15: 1,1-dimethylethyl (2S,5S)-2-(aminocarbonyl)-5-(4-{[(2-fluorophenyl)methyl]oxy}phenyl)-1-pyrrolidinecarboxylate (D15)

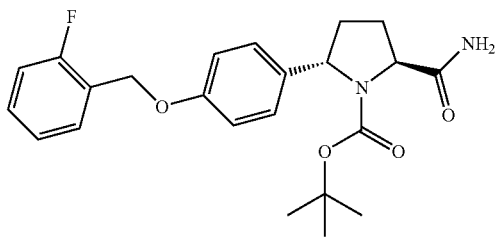

1-(Bromomethyl)-2-fluorobenzene (30 μl, 0.244 mmol) was added to a solution of 1,1-dimethylethyl (2S,5S)-2-(aminocarbonyl)-5-(4-hydroxyphenyl)-1-pyrrolidinecarboxylate (D14, 50 mg, 0.163 mmol) and potassium carbonate (34 mg, 0.244 mmol) in acetonitrile (0.5 ml). The mixture was stirred overnight at room temperature. Then ethyl acetate (20 mL) and water (10 mL) were added. The organic phase was dried over Na₂SO₄, filtered and evaporated under reduced pressure. The crude material was purified by chromatography on silica gel using cyclohexane/ethyl acetate (7:3 to 6:4) to afford the title compound (65 mg, 97%); R_f (cyclohexane:ethyl acetate=7:3): 0.19; MS: (ES/+) m/z: 437 [M+Na⁺], C23H27FN2O4 requires 414; R_t (HPLC): 5.28 min; ¹H NMR (400 MHz, DMSO-d₆) δ(ppm): 7.54-7.44 (m, 1H), 7.40-7.27 (m, 2H), 7.24-7.11 (m, 2H), 7.06-6.98 (m, 2H), 6.96-6.79 (m, 3H), 5.10-5.00 (m, 2H), 4.91 and 4.81 (d, d, 1H), 4.29 and 4.24 (d, d, 1H), 2.35-2.18 (m, 1H), 2.17-1.97 (m, 1H), 1.78-1.62 (m, 1H), 1.58-1.43 (m, 1H), 1.28 and 1.03 (s, s, 9H).

Description 16: 1-(1,1-dimethylethyl) 2-ethyl (2R)-5-oxo-1,2-pyrrolidinedicarboxylate (D16)

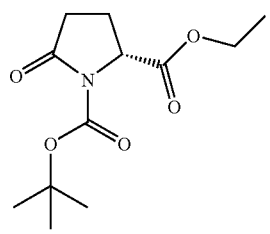

The title compound was synthesized (14 g, 71%) following a similar procedure as set out earlier in Description 1 starting from commercially available ethyl 5-oxo-D-prolinate (12 g, 75.6 mmol); R_f (cyclohexane:ethyl acetate=7:3): 0.25; R_t (HPLC) 3.94 min; ¹H NMR (400 MHz, DMSO-d6) δ (ppm): 4.61 (dd, 1H); 4.25 (q, 2H); 2.58-2.69 (m, 1H); 2.44-2.55 (m, 1H); 2.26-2.38 (m, 1H); 2.00-2.08 (m, 1H); 1.50 (s, 9H); 1.31 (t, 3H).

Description 17: Ethyl (2R)-2-({[(1,1-dimethylethyl)oxy]carbonyl}amino)-5-oxo-5-{4-[(phenylmethyl)oxy]phenyl}pentanoate (D17)

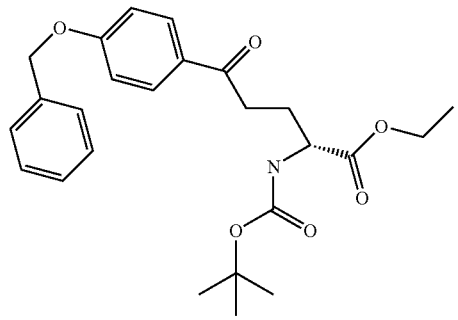

The title compound was synthesized (2.9 g, 16%) following a similar procedure as set out earlier in Description 2 starting from 1-(1,1-dimethylethyl) 2-ethyl (2R)-5-oxo-1,2-pyrrolidinedicarboxylate (D16, 10.5 g 40.8 mmol) and 4-iodophenyl phenylmethyl ether (13.34 g, 43 mmol); Rt (HPLC): 6.37 min; MS: (ES/+) 464 m/z: [M+Na⁺], C25H31NO6 requires 441; ¹H NMR (400 MHz, DMSO-d6) δ (ppm): 7.92 (d, 2H); 7.29-7.45 (m, 5H); 6.99 (d, 2H); 5.18 (bs, 1H); 5.12 (s, 2H); 4.29-4.4 (bm, 1H); 4.20 (q, 2H); 2.94-3.16 (m, 2H); 2.22-2.33 (m, 1H); 2.00-2.15 (m, 1H); 1.39 (s, 9H); 1.28 (t, 3H).

Description 18: Ethyl (2R)-5-{4-[(phenylmethyl)oxy]phenyl}-3,4-dihydro-2H-pyrrole-2-carboxylate (D18)

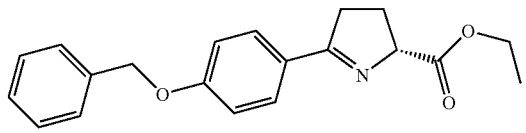

The title compound was synthesized following a similar procedure as set out earlier in Description 3 starting from ethyl (2R)-2-({[(1,1-dimethylethyl)oxy]carbonyl}amino)-5-oxo-5-{4-[(phenylmethyl)oxy]phenyl} pentanoate (D17, 2.9 g, 6.57 mmol). The crude material may be used without any further purification in the next step; R_t (HPLC): 3.80 min; MS: (ES/+) 324 m/z: [MH⁺], C20H21NO3 requires 323.

Description 19: Ethyl (5S)-5-{4-[(phenylmethyl)oxy]phenyl}-D-prolinate (D19)

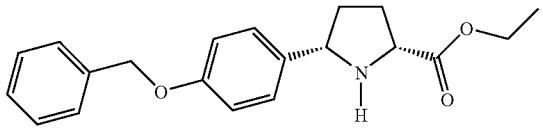

The title compound was synthesized (1.84 g, 86% over two steps) following a similar procedure as set out earlier in Description 4 using the crude material obtained from Description 18; Rt (HPLC): 4.03 min; MS: (ES/+) 326 m/z: [MH$^+$], C20H23NO3 requires 325; $^1$H NMR (500 MHz, CHCl3-d) δ (ppm): 7.30-7.47 (m, 7H), 6.96 (d, 2H), 5.06 (s, 2H), 4.23 (q, 2H), 4.15 (dd, 1H), 3.90 (dd, 1H), 2.17-2.28 (m, 1H), 2.07-2.17 (m, 2H), 1.61-1.76 (m, 1H), 1.31 (t, 3H).

Description 20: (5S)-5-{4-[(Phenylmethyl)oxy]phenyl}-D-proline (D20)

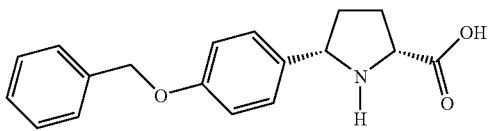

The title compound was synthesized following a similar procedure as set out earlier in Description 6 starting from ethyl (5S)-5-{4-[(phenylmethyl)oxy]phenyl}-D-prolinate (D19, 340 mg, 1.045 mmol); R$^t$ (HPLC): 3.62 min; MS: (ES/+) 298 m/z: [MH$^+$], C18H19NO3 requires 297.

Description 21: (5S)-1-{[(1,1-dimethylethyl)oxy]carbonyl}-5-{4-[(phenylmethyl)oxy]phenyl}-D-proline (D21)

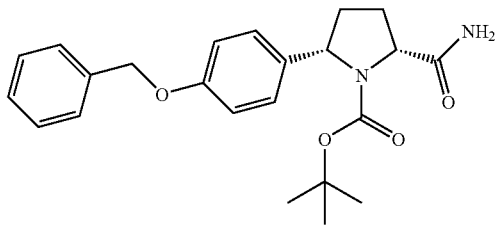

The title compound was synthesized (440 mg, quant. over two steps) following a similar procedure as set out earlier in Description 7 starting from (5S)-5-{4-[(phenylmethyl)oxy]phenyl}-D-proline (D20); Rt (HPLC): 5.77 min; MS: (ES/+) 420 m/z: [M+Na$^+$], C23H27NO5 requires 397; $^1$H-NMR (500 MHz, DMSO-d$_6$) δ (ppm): 12.55 (br.s., 1H); 6.65-6.78 (m, 7H); 6.95 (d, 2H); 5.10 (s, 2H); 4.60-4.84 (m, 1H); 4.23 (m, 1H); 2.10-2.30 (m, 2H); 1.63-1.95 (m, 2H); 1.05-1.39 (m, 9H).

Description 22: 1,1-dimethylethyl (2R,5S)-2-(aminocarbonyl)-5-{4-[(phenylmethyl)oxy]phenyl}-1-pyrrolidinecarboxylate (D22)

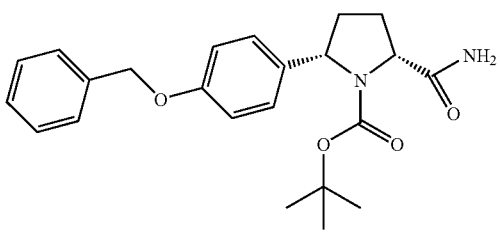

The title compound was synthesized (250 mg, 56%) following a similar procedure as set out earlier in Description 8 starting from (5S)-1-{[(1,1-dimethylethyl)oxy]carbonyl}-5-{4-[(phenylmethyl)oxy]phenyl}-D-proline (D21, 440 mg, 1.11 mmol); Rt (HPLC): 5.52 min; MS: (ES/+) 419 m/z: [M+Na$^+$], C23H28N2O4 requires 396.

Description 23: 1,1-dimethylethyl (2R,5S)-2-(aminocarbonyl)-5-(4-hydroxyphenyl)-1-pyrrolidinecarboxylate (D23)

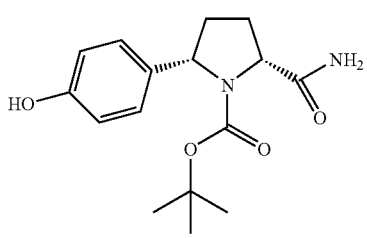

The title compound was synthesized (135 mg, quant.) following a similar procedure as set out earlier in Description 9 starting from 1,1-dimethylethyl (2R,5S)-2-(aminocarbonyl)-5-{4-[(phenylmethyl)oxy]phenyl}-1-pyrrolidinecarboxylate (D22, 175 mg, 0.44 mmol); Rt (HPLC): 3.63 min; MS: (ES/+) m/z: 329 [M+Na$^+$]. C16H22N2O4 requires 306; $^1$H NMR (300 MHz, d$_6$-DMSO) δ (ppm): 9.15 (bs, 1H); 7.40 (bm, 2H); 7.30 (s, 1H); 6.90 (s, 1H); 6.65 (d, 2H); 4.50-4.80 (m, 1H); 4.05-4.28 (m, 1H); 2.07-2.24 (m, 1H); 1.95-2.07 (m, 1H); 1.60-1.89 (m, 2H); 1.00-1.45 (m, 9H).

Description 24: 1,1-dimethylethyl (2R,5S)-2-(aminocarbonyl)-5-(4-{[(2-fluorophenyl)methyl]oxy}phenyl)-1-pyrrolidinecarboxylate (D24)

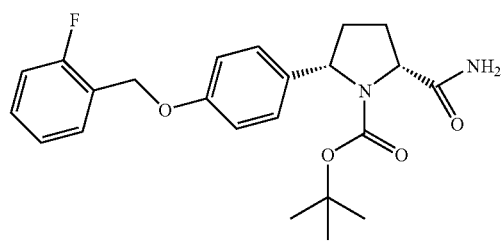

The title compound was synthesized (145 mg, 79%) following a similar procedure as set out earlier in Description 10 starting from 1,1-dimethylethyl (2R,5S)-2-(aminocarbonyl)-5-(4-hydroxyphenyl)-1-pyrrolidine carboxylate (D23, 130 mg, 0.44 mmol) and 1-(bromomethyl)-2-fluorobenzene (166 mg, 0.88 mmol); Rt (HPLC) 5.55; MS: (ES/+) 437 m/z: [M+Na$^+$], C23H27FN2O4 requires 414; $^1$H NMR (300 MHz, DMSO-d$_6$) δ(ppm): 7.48-7.63 (m, 3H); 4.30-4.45 (m, 2H); 4.18-4.29 (m, 2H); 6.90-7.06 (m, 3H); 5.10 (s, 2H); 4.56-4.82 (m, 1H); 4.10-4.18 (m, 1H); 2.12-2.26 (m, 1H); 1.98-2.12 (m, 1H); 1.60-1.95 (m, 2H); 0.98-1.42 (m, 9H).

Description 25: 1-[(4-bromophenoxy)methyl]-2-fluorobenzene (D25)

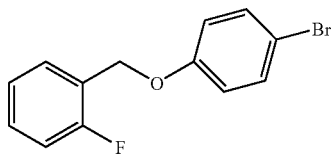

Procedure 1: To a solution of 4-bromophenol (502.08 g) dissolved in acetone (7322 mL) was added K$_2$CO$_3$ (570 g) and then benzylbromide (523 g). The mixture was heated under reflux for 2 hrs. The reaction mixture was then cooled at 25° C., filtered and the filter cake was washed with MTBE (1046 mL). The combined filtrate was concentrated to 1000 mL and MTBE (4184 mL) were added. The mixture was washed with an aqueous 1M NaOH solution (1464 mL), then with brine (1300 mL) and the organic phase was concentrated to dryness. THF (1300 mL) was added and the solvent was removed under reduced pressure to afford the title compound (902.1 g);

$^1$H NMR (400 MHz, DMSO-d6) δ(ppm): 7.54 (td, 1H); 7.46 (d, 2H); 7.42 (m, 1H); 7.23 (m, 2H); 7.01 (d, 2H); 5.13 (s, 2H).

D25 was also obtained as follows:

Procedure 2: A stirred mixture of 4-bromophenol (19.22 g, 111 mmol), orthofluorobenzyl bromide (20 g, 105.8 mmol) and potassium carbonate (21.9 g, 158.4 mmol) in acetone (280 ml) was heated at reflux for 6 hours. The reaction mixture was cooled to room temperature and filtered, washing the solid with TBME (40 ml). The combined filtrate and washings were concentrated under vacuum to a final volume of about 40 ml. The resulting solution was diluted with TBME (160 ml) and washed with 1M sodium hydroxide and brine, then concentrated under vacuum to an oil which slowly solidified to give the title compound (28.9 g).

$^1$H NMR (300 MHz, CHCl3-d). δ(ppm): 5.10 (s, 2H), 6.86 (m, 2H), 7.10 (m, 1H) 7.17 (m, 1H), 7.29 (m, 1H), 7.35 (m, 2H), 7.38 (m, 1H).

Description 26: methyl (2S)-2-({[(1,1-dimethylethyl)oxy]carbonyl}amino)-5-(4-{[(2-fluorophenyl)methyl]oxy}phenyl)-5-oxopentanoate (D26)

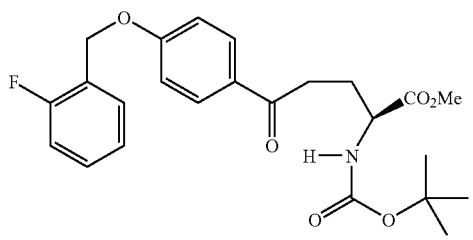

Procedure 1: To a stirred suspension of magnesium metal (90 g) in dry THF (600 mL) under a nitrogen atmosphere at room temperature was added iodine (0.3 g). The mixture was heated to an internal temperature of 64 +/−2° C. A solution of 1-[(4-bromophenoxy)methyl]-2-fluorobenzene (D25) (693 g) in THF (1500 mL) was added in two batches. Firstly 45 mL was added. Secondly, the remaining solution (1455 mL) was added dropwise. After addition, the reaction was heated at reflux for 1 h. The reaction mixture was cooled to room temperature. This reaction mixture was then added slowly to a solution of commercially available 1-tert-butyl 2-methyl (2S)-5-oxopyrrolidine-1,2-dicarboxylate (300 g) in THF (1500 mL) cooled to −60° C., maintaining the internal temperature below −60° C. The addition was completed in 2 hours. The reaction mixture was stirred for a further 15 minutes after addition. Isopropyl alcohol (300 mL) was then added dropwise whilst maintaining the temperature below −60° C. A mixture of aqueous saturated ammonium chloride solution/aqueous saturated sodium chloride solution (2/1; 900 mL) was added whilst maintaining the temperature at −50° C. Water (600 mL) was added to dissolve the yellow precipitate. The organic phase was separated and was washed with aqueous 13% NaCl solution (600 mL). The organic phase was concentrated to dryness. EtOAc (1500 mL) was then added and the solution was evaporated under reduced pressure to remove water. The residue was purified by chromatography on silica gel eluting with cyclohexane/ethyl acetate (90:10 to 8:2) to afford the title compound (287 g);

$^1$H NMR (600 MHz, DMSO-d6) δ(ppm): 7.93 (d, 2H); 7.57 (td, 1H); 7.44 (m, 1H); 7.27 (m, 3H); 7.14 (d, 2H); 5.24 (s, 2H); 4.04 (m, 1H); 3.61 (s, 3H); 3.03 (m, 2H); 1.94 (m, 2H); 1.38 (s, 9H).

D26 was also obtained as follows:

Procedure 2: To a mixture of magnesium turnings (12.79 g. 533 mol), a trace of iodine and 1,2-dibromoethane in THF (86 ml) at 70-75° C., a solution of (4-bromophenyl (2-fluorophenyl)methyl ether) (D25, 100 g, 355.6 mmol) in THF (216.25 ml) was added over about 2 hours. The mixture was heated for a further 2 hours at 70-75° C. then cooled to room temperature to give a solution of the Grignard reagent. A solution of 1-(1,1-dimethylethyl) 2-methyl (2S)-5-oxo-1,2-pyrrolidinedicarboxylate (43.25 g, 177.8 mmol) in THF (216.25 ml) was cooled to −60° C. and the solution of the Grignard reagent was added over 1 hour, then the mixture was stirred for 3 hours at −60° C. Isopropanol (43.25 ml) was added dropwise, followed by saturated aqueous ammonium chloride (86.5 ml) and brine (43.25 ml), then the mixture warmed to room temperature. Water (173 ml) and 50% acetic acid (50 ml) to pH 6-7, followed by ethyl acetate (129.7 ml). The layers were separated and the aqueous extracted with ethyl acetate (2×129.7 ml). The combined organic layers were washed with brine then concentrated under vacuum. The residue was stirred with hexane (216.2 ml), then the solid was filtered and washed with hexane. To the resulting solid, isopropanol (432.5 ml) was added and the mixture stirred at 45° C. for 15 minutes, then cooled to 5-10° C. and stirred for 2 hours. The solid was filtered, washed with isopropanol and dried to give the title compound as a solid.

$^1$H NMR (300 MHz, CHCl3-d): δ(ppm): 1.42 (s, 9H); 2.04 (m, 1H); 2.28 (m, 1H); 3.03 (m, 2H); 3.74 (s, 3H); 4.37 (m, 1H); 5.19 (b, 1H); 5.20 (s, 2H); 7.02 (d, 2H); 7.11 (t, 1H); 7.17 (t, 1H); 7.33 (m, 1H); 7.48 (t, 1H); 7.94 (d, 2H).

Description 27: methyl (2S)-5-{4-[(2-fluorobenzyl)oxy]phenyl}-3,4-dihydro-2H-pyrrole-2-carboxylate (D27)

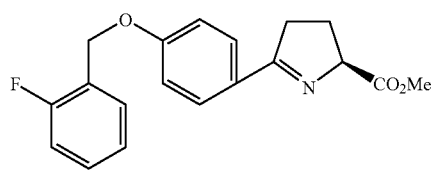

Procedure 1: To a solution of methyl (2S)-2-({[(1,1-dimethylethyl)oxy]carbonyl}amino)-5-(4-{[(2-fluorophenyl)methyl]oxy}phenyl)-5-oxopentanoate (D26) (243 g) in dry DCM (2430 mL) at 0° C. was added TFA (461 mL) dropwise. The mixture was allowed to warm to room temperature and stirred for 3 hrs. Solvent and the excess TFA were removed under vacuum and the resulting dark oil was stripped with EtOAc (2×1215 mL) and left overnight under a high vacuum. The title compound (392 g) was obtained as a red oil and used in the following step without any further purification; $^1$H NMR (400 MHz, DMSO-d6) δ(ppm): 8.16 (m, 2H); 7.60 (td, 1H); 7.46 (m, 1H); 7.34 (m, 2H); 7.27 (m, 2H); 5.32 (s, 2H); 5.25 (m, 1H), 3.77 (s, 3H); 3.57 (m, 2H); 2.60 (m, 1H); 2.34 (m, 1H).

D27 was also obtained as follows:

Procedure 2: A solution of methyl (2S)-2-({[(1,1-dimethylethyl)oxy]carbonyl}amino)-5-(4-{[(2-fluorophenyl)methyl]oxy}phenyl)-5-oxopentanoate (D26, 46 g, 103 mmol) in DCM (437 ml) was treated dropwise with trifluoroacetic acid (87.4 ml) at 0-5° C., then warmed to room temperature and stirred for 3 hours. The solution was cooled to 0-5° C. and sodium hydroxide solution added to a final pH of about 7. The aqueous layer was separated and extracted with DCM (13 ml), then the combined organic layers were washed with water, dried over sodium sulphate, then concentrated under vacuum to give the title compound as a solid (33.3 g).

1H NMR (300 MHz, CHCl3-d): δ(ppm): 2.35 (m, 2H); 2.95 (m, 1H); 3.12 (m, 1H); 3.78 (s, 3H); 4.89 (dd, 1H); 5.18 (s, 2H); 7.00 (d, 2H); 7.10 (m, 1H); 7.16 (m, 1H) 7.29 (m, 1H); 7.5 (t, 1H); 7.85 (d, 2H).

Description 28: Methyl (5R)-5-{4-[(2-fluorobenzyl)oxy]phenyl}-L-prolinate (D28)

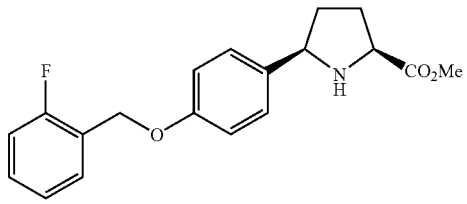

Procedure 1: Methyl (2S)-5-{4-[(2-fluorobenzyl)oxy]phenyl}-3,4-dihydro-2H-pyrrole-2-carboxylate (D27) (392 g) was dissolved in EtOAc (3160 mL) in a hydrogenation reactor. 5% platinum on carbon (Engelhard code 44379, moisture content ca. 50%, 15.8 g) was added, the reactor filled with hydrogen gas to a pressure of 2 atm and the reaction mixture was stirred for approximately 1.5 hours. The reactor was depressurised and the spent catalyst filtered through Celite, washing through with EtOAc (2×500 mL, then further 200 mL). Aqueous saturated NaHCO$_3$ solution (600 mL) was added to the filtrate, followed by aqueous 13% w/w Na$_2$CO$_3$ solution (up to pH=9, 100 mL). The mixture was stirred for 10 minutes and phases were then allowed to separate. The aqueous phase was removed and then the organic layer was washed once with brine (600 mL). The resulting solution was concentrated to dryness and the residue was purified by flash chromatography eluting with cyclohexane/ethyl acetate (1:1) to afford the title compound (133 g); $^1$H NMR (600 MHz, DMSO-d6) δ(ppm): 7.55 (dt, 1H); 7.41 (m, 1H); 7.34 (m, 2H); 7.23 (m, 2H); 6.97 (m, 2H); 5.12 (s, 2H); 4.09 (dd, 1H); 3.83 (dd, 1H); 3.66 (s, 3H); 2.97 (bs, 1H); 2.04 (m, 2H); 1.94 (m, 1H); 1.52 (m, 1H).

D 28 was also prepared as follows:

Procedure 2: A solution of methyl (2S)-5-(4-{[(2-fluorophenyl)methyl]oxy}phenyl)-3,4-dihydro-2H-pyrrole-2-carboxylate (D27, 34 g, 103.5 mmol) in ethyl acetate (272 ml) was placed in an autoclave and treated with trifluoroacetic acid (7.2 ml). 5% Platinum on carbon catalyst (1.7 g) was transferred as a slurry with ethyl acetate (68 ml) and the reaction was stirred at room temperature under 50 psi hydrogen pressure for 5 hours. The mixture was filtered through Hyflo, washing with ethyl acetate (272 ml), then the filtrate was washed with aq sodium carbonate solution and brine, dried over sodium sulphate, then concentrated under vacuum, and the residue dried to give the title compound as a crude oil (also containing some of the anti isomer), $^1$H NMR (300 MHz, CHCl3-d): δ(ppm): 1.7 (m, 1H); 2.18 (m, 4H); 3.75 (s, 3H); 3.91 (m, 1H); 4.15 (m, 1H); 5.13 (s, 2H); 6.96 (d, 2H); 7.07 (m, 1H); 7.15 (m, 1H); 7.30 (m, 1H); 7.38 (d, 2H); 7.5 (t, 1H).

EXAMPLES

Example 1

(5R)-5-(4-{[(2-Fluorophenyl)methyl]oxy}phenyl)-L-prolinamide (E1)

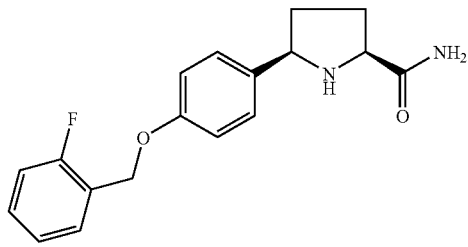

Procedure 1: A solution of methyl (5R)-5-(4-{[(2-fluorophenyl)methyl]oxy}phenyl)-L-prolinate (D28, 32.5 g, 98.6 mmol) in methanol (65 ml) was cooled to 0-10° C. A solution of ammonia in methanol (ca 11.2M) was added in four portions over 11 hours (175.4 ml, 43.8 ml, 43.8 ml. 43.8 ml) then the reaction stirred at 15-20° C. for 22 hours. Ammonia and methanol were removed under vacuum, then toluene (65 ml) was added and the mixture heated to 60-65° C. to give a solution, which was then concentrated under vacuum and the residue dried at 60° C. Toluene (130 ml) and methanol (0.32 ml) were added to the residue and the mixture heated to 70-75° C. The resulting solution was then cooled to 15-20° C. and stirred for 1 hour. The solid was filtered, washed with toluene and dried at 45-50° C. to give the title compound (21.8 g) as a solid.

$^1$H NMR (500 MHz, DMSO-d6) δ(ppm): 1.39 (m, 1H); 1.84 (m, 1H); 2.04 (m, 2H); 3.54 (m, 1H); 4.09 (m, 1H); 5.12 (s, 2H); 6.96 (d, 2H); 7.15 (m, 1H); 7.25 (m, 2H); 7.34 (d, 2H); 7.41 (m, 2H); 7.55 (t, 1H).

E1 was also prepared as follows:

Procedure 2: Methyl (5R)-5-{4-[(2-fluorobenzyl)oxy]phenyl}-L-prolinate (D28) (127 g) was dissolved in 7N NH$_3$ solution in MeOH (1016 mL) and the mixture was stirred at room temperature for 24 hrs. Further 7N NH$_3$ solution in MeOH (63 mL) was added and the mixture stirred for a further 15 hours. The solvent was removed under reduced pressure and MeOH (635 mL) was added. The solution was evaporated to dryness and the white solid obtained was left under high vacuum over the weekend. The white solid was suspended in a mixture of MTBE/Toluene 1:1 (254 mL) at 20° C. and stirred for 1 hr. The suspension was filtered and the solid washed with MTBE (254 mL). The white solid was dried at 40° C. overnight under vacuum affording 122.4 g of material. This material was resuspended in a mixture of MTBE/toluene 1:1 (245 mL) and stirred at room temperature for 1 hour. The mixture was filtered and the solid was washed with MTBE (245 mL). The white solid obtained was dried at 40° C. overnight under vacuum to give the title compound (109 g). $^1$H NMR (600 MHz, DMSO-d6) δ(ppm): 7.54 (td, 1H); 7.41 (m, 1H); 7.38 (m, 2H); 7.34 (d, 2H); 7.24 (m, 2H); 7.13 (bs, 1H); 6.96 (d, 2H); 5.12 (s, 2H); 4.09 (dd, 1H); 3.55 (dd, 1H); 3.24 (bs, 1H); 2.07 (m, 1H); 2.00 (m, 1H); 1.85 (m, 1H); 1.40 (m, 1H).

Example 2

(5R)-5-(4-{[(2-fluorophenyl)methyl]oxy}phenyl)-L-prolinamide hydrochloride (E2)

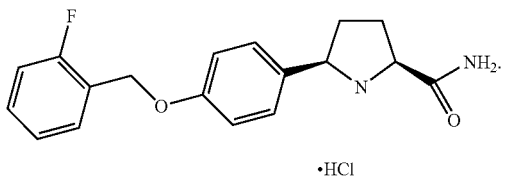

·HCl

Procedure 1: To a solution of 1,1-dimethylethyl (2S,5R)-2-(aminocarbonyl)-5-(4-{[(2-fluorophenyl)methyl]oxy}phenyl)-1-pyrrolidinecarboxylate (D10, 51 mg, 0.123 mmol) in a mixture of ethyl acetate (0.9 ml) and methanol (1 ml) was added acetylchloride (28 µl, 2.5 eq) at 0° C. The mixture was shaken for 1.5 h and slowly allowed to warm to room temperature. After evaporating the solvent, the residue was triturated with diethyl ether to afford the title compound as a white solid (42 mg, quant.); Chiral HPLC: Column: chiralcel OD 10 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 22 min; ret. time: 12.0 min. $[\alpha]_D$=−30.5°. MS: (ES/+) m/z: 315 [MH$^+$], C18H19FN2O2 requires 314; $^1$H NMR (400 MHz, DMSO-d6) δppm 10.19 (br. s., 1H), 8.13 (br. s., 1H), 7.94 (s, 1H), 7.60-7.77 (m, 1H), 7.51 (dt, 1H), 7.43 (d, 2H), 7.34-7.41 (m, 1H), 7.23 (d, 1H), 7.18 (dd, 1H), 7.05 (d, 2H), 5.13 (s, 2H), 4.49-4.60 (m, 1H), 4.19-4.28 (m, 1H), 2.17-2.38 (m, 2H), 2.05-2.16 (m, 1H), 1.92-2.03 (m, 1H).

Example 2 was also prepared as follows:

Procedure 2: ((5R)-5-(4-{[(2-fluorophenyl)methyl]oxy}phenyl)-L-prolinamide) (E1, 109 g) was dissolved in DCM (654 mL) and Et$_2$O (654 mL) was added at room temperature. HCl 1N in Et$_2$O (380.4 mL) was added dropwise at room temperature. The suspension was cooled to 0° C. and stirred at this temperature for 1 hr. The solid was filtered, washed with Et$_2$O (2×327 mL) and dried at 40° C. under vacuum overnight to afford Form 1 crystals of the title compound (121.24 g). $^1$H NMR (600 MHz, DMSO-d6) δ(ppm): 10.72 (bs, 1H); 8.10 (bs, 1H); 8.08 (s, 1H); 7.72 (s, 1H); 7.56 (td, 1H); 7.49 (d, 2H); 7.43 (qd, 1H); 7.25 (m, 2H); 7.10 (d, 2H); 5.17 (s, 2H); 4.61 (dd, 1H); 4.30 (dd, 1H); 2.32 (m, 2H); 2.16 (m, 1H); 2.02 (m, 1H).

Procedure 3: ((5R)-5-(4-{[(2-fluorophenyl)methyl]oxy}phenyl)-L-prolinamide) (E1, 10 g, 31.8 mmol) was dissolved in DCM (50 ml) and stirred with charcoal (1 g), then filtered, washing with DCM (30 ml). The residue was concentrated under vacuum, removing about 20 ml of DCM. Ether (60 ml) was added, followed by a solution of HCl in ether (0.84N, 40 ml), and the mixture was then stirred at 20-25° C. for 30 min, then cooled to 0-5° C. and stirred for 2 hours. The solid was filtered, washed with ether, then dried at room temperature to give Form 1 crystals of title compound (10.25 g).

$^1$H NMR (300 MHz, DMSO-d$_6$) δ(ppm): 2.04 (m, 1H); 2.18 (m, 1H); 2.32 (m, 2H); 4.34 (m, 1H); 4.64 (m, 1H); 5.18 (s, 2H); 7.10 (d, 2H); 7.25 (m, 2H); 7.40-7.60 (m, 4H); 7.77 (s, 1H); 8.24 (s, 1H); 11.03 (b, 1H).

Procedure 4: In a round bottom flask, a solution of ((5R)-5-(4-{[(2-fluorophenyl)methyl]oxy}phenyl)-L-prolinamide) (E1, 1.4 g, 4.45 mmol) in ethylacetate (14 ml) and MeOH (2.5 ml) at 0° C. was treated with HCl 1M in diethylether (1.1 eq, 4.89 ml). The precipitation occurred quite soon and the mixture was stirred at 0° C. for 1 h. The mixture was then diluted with dry diethylether (10 ml) and then filtered on a Gooch filter (porosity 4, diameter 5 cm). The cake was washed on the filter with dry diethylether (2×20 ml) and the white solid thus obtained was transferred into a round bottom flask, dried under high vacuum at 40° C. for 2 h and then at room temperature for 18 hours. A white solid was obtained (1.51 g) of Form 1 crystals of the title compound.

Procedure 5: ((5R)-5-(4-{[(2-fluorophenyl)methyl]oxy}phenyl)-L-prolinamide) (E1, 25 g, 79.5 mmol) was dissolved in ethyl acetate (750 ml) and stirred with charcoal (2.5 g), then filtered, washing with ethyl acetate (125 ml). To the filtrate and washings, a solution of HCl in ether (1N, 103 ml), was added over 30 minutes at 20-25° C. and the mixture was then stirred at 20-25° C. for 30 min, then cooled to 0-5° C. and stirred for 2 hours. The solid was filtered, washed with ethyl acetate (2×70 ml), then dried at room temperature to give Form 1 crystals of the title compound. (25.5 g).

Unique and discriminating peaks of Form 1 of the title compound of Example 2 have been identified and are illustrated in the table below:

| Position [° 2 Th.] | d-spacing [Å] |
| --- | --- |
| 4.7 | 18.6 |
| 9.5 | 9.3 |
| 12.6 | 7.0 |
| 14.3 | 6.2 |
| 19.2 | 4.6 |
| 20.3 | 4.4 |
| 20.9 | 4.2 |
| 24.0 | 3.7 |
| 26.4 | 3.4 |

Melting point: 230° C.

Example 3

(5S)-5-(4-{[(2-fluorophenyl)methyl]oxy}phenyl)-L-prolinamide hydrochloride (E3)

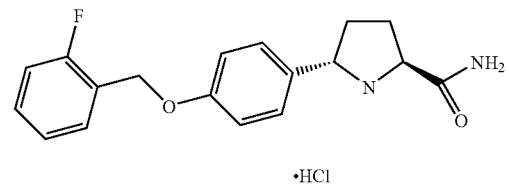

·HCl

The title compound was synthesized (51 mg, 100%) following a similar procedure to that described for Example 2, Procedure 1, from 1,1-dimethylethyl (2S,5S)-2-(aminocarbonyl)-5-(4-{[(2-fluorophenyl)methyl]oxy}phenyl)-1-pyrrolidinecarboxylate (D15, 62 mg, 0.15 mmol); R$_t$ (HPLC): 3.54 min; Chiral HPLC. Column: chiralpak AD-H 5 um, 250×4.6 mm Mobile phase: A: n-Hexane; B: Isopropanol. Gradient: isocratic 30% B. Flow rate: 0.8 ml/min. UV wavelength range: 200-400 nm. Analysis time: 15 min. ret. time: 10.4 min; MS: (ES/+) m/z: 315 [MH$^+$], C18H19FN2O2 requires 314; $^1$H NMR (500 MHz, DMSO-d6) δ(ppm): 9.37-9.13 (br. s., 2H), 8.01 (s, 1H), 7.68 (s, 1H), 7.55 (t, 1H), 7.49 (d, 2H), 7.45-7.37 (m, 1H), 7.29-7.20 (m, 2H), 7.08 (d, 2H), 5.17 (s, 2H), 4.62 (dd, 1H), 4.31 (t, 1H), 2.59-2.50 (m, 1H), 2.37-2.26 (m, 1H), 2.18-2.03 (m, 1H), 2.01-1.88 (m, 1H).

Example 4

(5S)-5-(4-{[(2-fluorophenyl)methyl]oxy}phenyl)-D-prolinamide hydrochloride (E4)

Example 5

(5R)-5-(4-{[(2-fluorophenyl)methyl]oxy}phenyl)-D-prolinamide hydrochloride (E5)

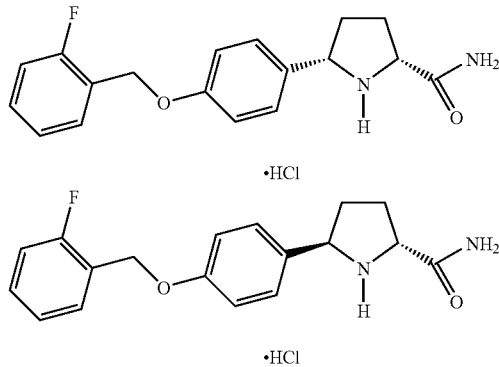

To a solution of 1,1-dimethylethyl (2R,5S)-2-(aminocarbonyl)-5-(4-{[(2-fluorophenyl)methyl]oxy}phenyl)-1-pyrrolidinecarboxylate (D24, 145 mg, 0.37 mmol) in DCM (6 ml) was added TFA (1.5 ml) dropwise at 0° C. The mixture was stirred for 1 h under these conditions. After evaporating the solvent, the resulting crude material was purified by SCX cartridge, to afford the title compounds (100 mg, 92%) as a mixture of diastereoisomers.

The diastereoisomers were separated using chiral semi-preparative HPLC: Column: chiralpak AD-H; Mobile phase: n-Hexane:Ethanol=70/30; Flow rate: 13 ml/min; UV wavelength range: 225 nm; Analysis time: 25 min.

Analytical chromatographic conditions: Chiral HPLC: Column: chiralpak AD-H 5 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 30 min; R$_t$: 14.02 min (E4); R$_t$: 16.12 min (E3)

E4 (69.5 mg): R$_t$ (HPLC): 3.60 min. Chiral HPLC: Column: chiralcel OD 10 um, 250×4.6 mm; Mobile phase: A: n-Hexane; B: Ethanol; Gradient: isocratic 30% B; Flow rate: 0.8 ml/min; UV wavelength range: 200-400 nm; Analysis time: 22 min. R$_t$: 17.6 min. [α]$_D$=+30.7°. $^1$H-NMR (400 MHz, DMSO-d$_6$) δ(ppm): 10.19 (br.s., 1H); 8.13 (br.s., 1H); 7.94 (s, 1H); 7.60-7.77 (m, 1H); 7.51 (dt, 1H); 7.43 (d, 2H); 7.34-7.41 (m, 1H); 7.23 (d, 1H); 7.18 (dd, 1H); 7.05 (d, 2H); 5.13 (s, 2H); 4.49-4.60 (m, 1H); 4.19-4.28 (m, 1H); 2.17-2.38 (m, 1H); 2.05-2.16 (m, 1H); 1.92-2.03 (m, 1H).

E5 (32 mg): R$_t$ (HPLC): 3.55 min. Chial HPLC: Column: chiralpak AD-H 5 um, 250×4.6 mm; Mobile phase: A: n-Hexane; B: Isopropanol; Gradient: isocratic 30% B; Flow rate: 0.8 ml/min; UV wavelength range: 200-400 nm; Analysis time: 15 min; R$_t$: 8.4 min. [α]$_D$=+24.3°. $^1$H-NMR (400 MHz, DMSO-d$_6$) δ (ppm): 9.25 (br.s., 2H); 8.01 (s, 1H); 7.68 (s, 1H); 7.55 (t, 1H); 7.49 (d, 2H); 7.37-7.45 (m, 1H); 7.20-7.29 (m, 2H); 7.08 (d, 2H); 5.17 (s, 2H); 4.62 (dd, 1H); 4.31 (t, 1H); 2.50-2.59 (m, 1H); 2.26-2.37 (m, 1H); 2.03-2.18 m, 1H); 1.88-2.01 (m, 1H).

Example 6

(5R)-5-(4-{[(2-fluorophenyl)methyl]oxy}phenyl)-L-prolinamide methanesulfonate (E6)

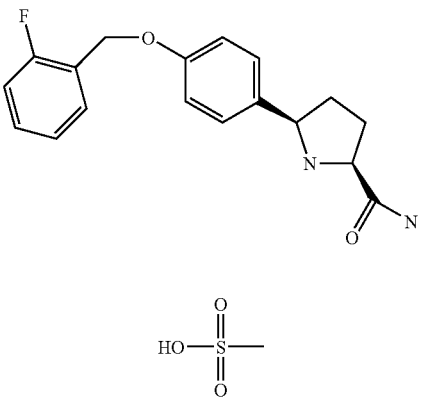

EtOAc (6 ml) was added to (5R)-5-(4-{[(2-Fluorophenyl)methyl]oxy}phenyl)-L-prolinamide (E1, 300 mg) and this was heated at 60° C. for an hour to dissolve the compound. Then methanesulfonic acid (65 μl, 1.05 eq) was added to the solution and as soon as the acid was added, the solution went cloudy. This was then left to temperature cycle (0-40° C.) for 2 days. The compound was isolated by filtration as a white solid, washed with EtOAc and dried in vacuo at 40° C. over-week-end to afford 335 mg of the title compound.

Melting point: 192° C.

Biological Assay

The ability of the compounds of the invention to modulate the voltage-gated sodium channel subtype NaV 1.3 may be determined by the following assay.

Cell Biology

Stable cell lines expressing hNaV1.3 channels were created by transfecting CHO cells with the pCIN5-hNav1.3 vector using the lipofectamine (Invitrogen) transfection method. pCIN5 is a bicistronic vector for the creation of mammalian cell lines that predisposes all neomycin resistant cells to express recombinant protein (see Rees S., Coote J., Stable J., Goodson S., Harris S. & Lee M. G. (1996) Biotechniques, 20, 102-112) by virtue of the recombinant cDNA being linked to the neomycin-selectable marker cDNA downstream of the CMV promoter (for full details see Chen Y H, Dale T J, Romanos M A, Whitaker W R, Xie X M, Clare J J. Cloning, distribution and functional analysis of the type III sodium channel from human brain Eur J Neurosci, 2000 December; 12, 4281-9). Cells were cultured in Iscove's modified Dulbecco's medium (Invitrogen) containing, 10% fetal bovine serum, 1% L-glutamine, 1% Penicillin-Streptomycin (Invitrogen), 1% non-essential amino acids, 2% H-T supplement and 1% G418 (Invitrogen) and maintained at 37° C. in a humidified environment containing 5% CO2 in air. Cells were liberated from the T175 culture flask for passage and harvesting using Versene (Invitrogen).

Cell Preparation

Cells were grown to 60-95% confluence in a T75 flask. Cells were lifted by removing the growth media and incubating with 1.5 ml of warmed (37° C.) Versene (Invitrogen, 15040-066) for 6 min. Lifted cells were suspended in 10 ml of PBS (Invitrogen, 14040-133). Cell suspension was then placed into a 10-ml centrifuge tube and centrifuged for 2 min at 700 rpm. After centrifugation, the supernatant was removed and the cell pellet was resuspended in 3 ml of PBS.

Electrophysiology

Currents were recorded at room temperature (21-23° C.) using the IonWorksHT planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential of −90 mV to 0 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 100, KCl 40 mM, MgCl2 3.2, EGTA 3, HEPES 5, adjusted to pH 7.25. Amphotericin was prepared as 30 mg/ml stock solution and diluted to a final working concentration of 0.1 mg/ml in internal buffer solution. The external solution was Dulbecco's PBS (Invitrogen) and contained the following (in mM): CaCl2 0.90, KCl 2.67, K3PO4 1.47, MgCl2 0.50, NaCl 138, Na3PO4 8.10, with a pH of 7.4. Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using both seal resistance (>40 MΩ) and peak current amplitude (>200pA) in the absence of compound to eliminate unsuitable cells from further analysis. Paired comparisons between pre-drug and post-drug additions were used to determine the inhibitory effect of each compound. The concentrations of compounds required to inhibit current elicited by the 1$^{st}$ depolarising pulse by 50% (tonic pIC50) were determined by fitting of the Hill equation to the concentration response data. In addition the use-dependent inhibitory properties of the compounds were determined by assessing the effect of compounds on the 10$^{th}$ versus 1$^{st}$ depolarising pulse. The ratio of the 10$^{th}$ over 1$^{st}$ pulse was calculated in the absence and presence of drug and the % use-dependent inhibition calculated. The data was fitted using the same equation as for the tonic pIC$_{50}$ and the concentration producing 15% inhibition (use-dependent pUD$_{15}$) calculated.

The compounds of examples 2 to 5 were tested in the above assay and gave pUD$_{15}$ values greater than 5.0.

The invention claimed is:

1. A compound of formula (I),

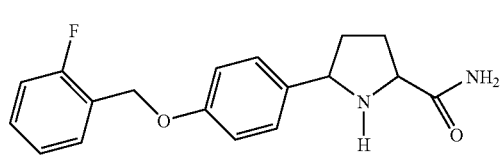

or a pharmaceutically acceptable salt thereof.

2. The compound

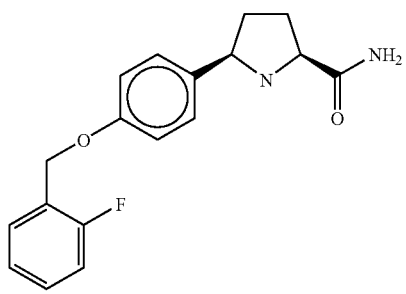

or a pharmaceutically acceptable salt thereof.

3. (5R)-5-(4-{[(2-fluorophenyl)methyl]oxy}phenyl)-L-prolinamide hydrochloride.

4. A pharmaceutical composition comprising a compound as claimed in claim 1, and a pharmaceutically acceptable carrier.

5. A process to prepare a compound as claimed in claim 1 comprising reacting a compound of formula (II)

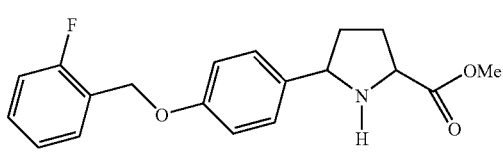

with a solution of ammonia in a suitable solvent.

6. (5R)-5-(4-{[(2-fluorophenyl)methyl]oxy}phenyl)-L-prolinamide.

7. A compound according to claim 3, wherein said compound is characterized by an XRPD pattern having characteristic peaks at the following positions: 4.7±0.15 (°2θ), 9.5±0.15 (°2θ), 12.6±0.15 (°2θ), 14.3±0.15 (°2θ), 19.2±0.15 (°2θ), 20.3±0.15 (°2θ), 20.9±0.15 (°2θ), 24.0±0.15 (°2θ), 26.4 ±0.15 (°2θ).

8. A method of treating inflammatory pain or neuropathic pain in a mammal comprising administering an effective amount of a compound according to claim 1 wherein said treating consists of at least one selected from the following:

(a) treating an established condition; and (b) suppressing or ameliorating symptoms.

9. A method of treating neuropathic pain in a mammal comprising administering an effective amount of a compound according to claim 1 wherein said treating consists of at least one selected from the following:

(a) treating an established condition; and (b) suppressing or ameliorating symptoms.

10. A method according to claim 8 wherein the mammal is a human.

11. A pharmaceutical composition comprising a compound as claimed in claim 3, and a pharmaceutically acceptable carrier.

12. A method of treating inflammatory pain or neuropathic pain in a mammal comprising administering an effective amount of a compound according to claim 3 wherein said treating consists of at least one selected from the following:

(a) treating an established condition; and (b) suppressing or ameliorating symptoms.

13. A method of treating neuropathic pain in a mammal comprising administering an effective amount of a compound according to claim 3 wherein said treating consists of at least one selected from the following:

(a) treating an established condition; and (b) suppressing or ameliorating symptoms.

14. A method according to claim 13 wherein the mammal is a human.

* * * * *